United States Patent
Nagamatsu et al.

(10) Patent No.: US 10,087,468 B2
(45) Date of Patent: *Oct. 2, 2018

(54) ADDITIVE FOR BIOETHANOL FERMENTATION PROCESS AND METHOD FOR PRODUCING BIOETHANOL

(71) Applicant: SAN NOPCO LTD., Kyoto-shi, Kyoto (JP)

(72) Inventors: Hironori Nagamatsu, Kyoto (JP); Tsutomu Miyata, Kyoto (JP)

(73) Assignee: SAN NOPCO LTD., Kyoto (JP)

( * ) Notice: Subject to any disclaimer, the term of this patent is extended or adjusted under 35 U.S.C. 154(b) by 125 days.

This patent is subject to a terminal disclaimer.

(21) Appl. No.: 14/889,580

(22) PCT Filed: Feb. 19, 2014

(86) PCT No.: PCT/JP2014/053948
§ 371 (c)(1),
(2) Date: Nov. 6, 2015

(87) PCT Pub. No.: WO2015/025538
PCT Pub. Date: Feb. 26, 2015

(65) Prior Publication Data
US 2016/0090609 A1    Mar. 31, 2016

(30) Foreign Application Priority Data

Aug. 20, 2013   (JP) ................................ 2013-170798

(51) Int. Cl.
| | |
|---|---|
| *C12P 7/06* | (2006.01) |
| *C12P 7/10* | (2006.01) |
| *C07C 43/04* | (2006.01) |
| *C12N 1/22* | (2006.01) |
| *C12N 1/38* | (2006.01) |

(52) U.S. Cl.
CPC ................ *C12P 7/06* (2013.01); *C07C 43/04* (2013.01); *C12N 1/22* (2013.01); *C12N 1/38* (2013.01); *C12P 7/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | | |
|---|---|---|---|---|---|
| 5,843,734 | A | * | 12/1998 | Shonaka ............ | B01D 19/0404 435/106 |
| 2010/0197559 | A1 | * | 8/2010 | Kotera ................ | C07C 41/03 510/506 |
| 2011/0171707 | A1 | * | 7/2011 | Holt .................... | C12N 1/18 435/161 |
| 2012/0225465 | A1 | * | 9/2012 | Pimentel ............. | C12P 7/10 435/165 |
| 2014/0171670 | A1 | * | 6/2014 | Jenkins ............... | C11B 13/00 554/19 |
| 2016/0128986 | A1 | * | 5/2016 | O'Neil ................ | A61K 39/00 424/490 |
| 2017/0349916 | A1 | * | 12/2017 | Nagamatsu ......... | C12P 7/06 |

FOREIGN PATENT DOCUMENTS

| | | | |
|---|---|---|---|
| JP | 4-59834 | A | 2/1992 |
| JP | 2008-297229 | A | 12/2008 |
| JP | 2009-108430 | A | 5/2009 |
| JP | 2009-185413 | A | 8/2009 |
| JP | 2012-075378 | A | 4/2012 |
| JP | 2014-083466 | A * | 5/2014 |

OTHER PUBLICATIONS

Notification of Transmittal of Translation of the International Preliminary Report on Patentability dated Mar. 3, 2016 (Form PCT/IB/338, form PCT/IB/373 and PCT/ISA/237), issued in International Patent Application No. PCT/JP2014/053948. (8 pages).
International Search Report dated May 27, 2014, issued in counterpart Application No. PCT/JP2014/053948 (2 pages).
Notice of Reasons for Refusal dated Jul. 25, 2017, issued in Japanese Patent Aoolication No. 2015-532719 with translation.

* cited by examiner

*Primary Examiner* — Joseph D Anthony
(74) *Attorney, Agent, or Firm* — Westerman, Hattori, Daniels & Adrian, LLP

(57) ABSTRACT

An object of the present invention is to provide an additive that can improve the production efficiency. The present invention is an additive for a bioethanol fermentation process comprising a polyoxyalkylene compound (A) having a Griffin's HLB value in the range of 0 to 6 and a polyoxyalkylene polyol (B). The compound (A) is preferably a mixture of a compound represented by a general formula (1) and a compound represented by a general formula (2). R1O-(AO)m-R2 (1). R3O-(AO)n-(EO)p-R4 (2). R1 and R3 represent alkyl or alkenyl, R2 and R4 represent a hydrogen atom or a monovalent organic group, AO represents oxyalkylene having a carbon number of 3 to 18, or a reaction residue of glycidol, an alkyl glycidyl ether or alkenyl glycidyl ether, EO represents oxyethylene, m and n are 1 to 100, and p is 3 to 10.

5 Claims, No Drawings

ADDITIVE FOR BIOETHANOL FERMENTATION PROCESS AND METHOD FOR PRODUCING BIOETHANOL

TECHNICAL FIELD

The present invention relates to an additive for a bioethanol fermentation process and a method for producing bioethanol.

BACKGROUND ART

Bioethanol is produced by alcohol fermentation, using sugar cane, corn, lignocellulose and the like, as a raw material (Patent Document 1, Non-Patent Document 1).

CITATION LIST

Patent Document

[Patent Document 1] JP 2008-297229 A

Non-Patent Document

[Non-Patent Document 1] "Biseibutsu-ni-yoru-Kagakuhannou" (document, for guidance, Science No. 240, for junior high school and high school, and school for the blind, the deaf and the handicapped, November, 2003, published by Kagoshima Prefectural Institute For Education Research)

SUMMARY OF INVENTION

Problems to be Solved by the Invention

In the method described in Non-Patent Document 1, when production is performed on a commercial scale, there is a problem that the production efficiency is low. In addition, even in the method (or device) described in Patent Document 1, there is a problem that the production efficiency is not enough.

An object of the present invention is to provide an additive that can solve the above problems (i.e., can improve the production efficiency).

Means for Solving the Problems

The present inventors have intensively studied to attain the above object, and consequently arrived at the present invention.

More specifically, the gist of the characteristics of the additive for a bioethanol fermentation process of the present invention is to contain a polyoxyalkylene compound (A) having a Griffin's HLB value in the range of 0 to 6 and a polyoxyalkylene polyol (B).

The gist of the characteristics of the method for producing bioethanol of the present invention, in which at least one selected from the group consisting of saccharide raw materials, starch raw materials and wooden (or cellulose) raw materials is used as a raw material, is to include a fermentation step of fermenting the raw material by adding the additive for a bioethanol fermentation process to a fermentation liquid.

Advantageous Effects of Invention

The additive for a bioethanol fermentation process of the present invention exhibits markedly excellent production efficiency in a bioethanol fermentation process.

Bioethanol can be produced with high production efficiency by the method for producing bioethanol of the present invention.

MODE FOR CARRYING OUT THE INVENTION

Examples of the polyoxyalkylene compound (A) having a Griffin's HLB value in the range of 0 to 6 include a polyoxyalkylene alkyl compound (A1) represented by a general formula (1), a polyoxyalkylene alkyl compound (A2) represented by a general formula (2), and mixtures thereof.

$$R^1O\text{-}(AO)_m\text{-}R^2 \qquad (1)$$

$$R^3O\text{-}(AO)_n\text{-}(EO)_p\text{-}R^4 \qquad (2)$$

Griffin's HLB value is the value calculated by the Griffin method (for example, "Shin-Kaimenkasseizai-Nyumon" authored by Takehiko Fujimoto, published by Sanyo Chemical Industries, Ltd., pages 128 to 131, 1981; English version: New Introduction to Surface Active Agents, T. Fujimoto, Sanyo Chemical Industries, Ltd., pages 128 to 131). In the calculation, only oxyethylene groups are defined as hydrophilic groups, and the other portions are defined as hydrophobic groups. In addition, when the polyoxyalkylene compound (A) is a mixture composed of a plurality of types of polyoxyalkylene compounds, HLB does not indicate an average of the plurality of types of polyoxyalkylene compounds, but the respective values of the polyoxyalkylene compounds.

$R^1$ and $R^3$ represent an alkyl group or alkenyl group having a carbon number of 4 to 28, $R^2$ and $R^4$ represent a hydrogen atom or a monovalent organic group having a carbon number of 1 to 24, AO represents an oxyalkylene group having a carbon number of 3 to 18, a reaction residue of glycidol or an alkenyl glycidyl ether or alkenyl glycidyl ether having a carbon number of 4 to 18, EO represents an oxyethylene group, m and n are an integer of 1 to 100, and p is an integer of 3 to 10.

Examples of the alkyl group or alkenyl group having a carbon number of 4 to 28 ($R^1$, $R^3$) include an alkyl group (R) and an alkenyl group (R').

Examples of the alkyl group (R) include butyl, t-butyl, octyl, 2-ethylhexyl, dodecyl, tetradecyl, hexadecyl, octadecyl, and the like.

Examples of the alkenyl group (R') include butenyl, octenyl, isooctenyl, dodecenyl, octadecenyl, and the like.

Among them, alkyl groups (R) are preferred from the viewpoint of production efficiency.

Among the hydrogen atom or the monovalent organic group having a carbon number of 1 to 24 ($R^2$, $R^4$), examples of the monovalent organic group having a carbon number of 1 to 24 include alkyl groups (R), alkenyl groups (R'), acyl groups (—COR), aroyl groups (—COR'), N-alkylcarbamoyl groups (—CONHR), N-alkenylcarbamoyl groups (—CONHR'), alkylcarbonylamino groups (—NHCOR), alkenylcarbonylamino groups (—NHCOR'), alkylcarboxyamino groups (alkylcarbamate groups, —NHCOOR), and alkenylcarboxyamino groups (alkenylcarbamate groups, —NHCOOR'). Among chemical formulae written in the parentheses, R and R' correspond to the alkyl group (R) and alkenyl group (R'), respectively.

Among the hydrogen atom or the monovalent organic groups having a carbon number of 1 to 24 ($R^2$, $R^4$), a hydrogen atom or alkyl group (R) is preferred from the viewpoint of production efficiency.

Among the oxyalkylene group having a carbon number of 3 to 18, and the reaction residue of glycidol or an alkenyl glycidyl ether or alkenyl glycidyl ether having a carbon number of 4 to 18 (AO), examples of the oxyalkylene group having a carbon number of 3 to 13 include oxypropylene, oxybutylene, oxyisobutylene, oxy-1,2-decylene, oxy-1,12-dodecylene, oxy-1,2-dodecylene, oxy-1,2-octadecylene, and the like.

In addition, among (AO), examples of the alkyl glycidyl ether having a carbon number of 4 to 21 include methyl glycidyl ether, ethyl glycidyl ether, butyl glycidyl ether, 2-ethyl hexyl glycidyl ether, dodecyl glycidyl ether, octadecyl glycidyl ether, and the like.

Moreover, among (AO), examples of the alkenyl glycidyl ether having a carbon number of 5 to 21 include vinyl glycidyl ether, butenyl glycidyl ether, 2-ethyl hexenyl glycidyl ether, dodecenyl glycidyl ether, octadecenyl glycidyl ether, and the like.

m and n are an integer of 1 to 100, preferably an integer of 2 to 75, and further preferably an integer of 3 to 60.

p is an integer of 3 to 10, preferably an integer of 4 to 8, and further preferably an integer of 4 to 6.

When the polyoxyalkylene compound (A) is a mixture of the polyoxyalkylene alkyl compound (A1) represented by the general formula (1) and the polyoxyalkylene alkyl compound (A2) represented by the general formula (2), the content of the polyoxyalkylene alkyl compound (A1) represented by the general formula (1) is preferably 0.1 to 90% by weight, further preferably 1 to 85% by weight, and particularly preferably 5 to 80% by weight, based on the weight of the polyoxyalkylene compound (A). In this case, the content of the polyoxyalkylene alkyl compound (A2) represented by the general formula (2) is preferably 10 to 99.9% by weight, further preferably 15 to 99% by weight, and particularly preferably 20 to 95% by weight, based on the weight of the polyoxyalkylene compound (A).

Examples of the polyoxyalkylene polyol (B) preferably include at least one selected from the group consisting of a polyoxypropylene polyol (B1) represented by a general formula (3), a polyoxyethylene polyoxypropylene polyol (B2) represented by a general formula (4), a polyoxyethylene polyoxypropylene polyol (B3) represented by a general formula (5), a polyoxyethylene polyoxypropylene polyol (B4) represented by a general formula (6) and a polyoxyethylene polyoxypropylene polyol (B5) represented by a general formula (7).

$$R^5-[-(PO)_q-H]_r \quad (3)$$

$$R^6-[-(EO)_s-(PO)_q-H]_r \quad (4)$$

$$R^7-[-(PO)_q-(EO)_3-H]_r \quad (5)$$

$$R^8-[-(EO)_s-(PO)_q-(EO)_t-H]_r \quad (6)$$

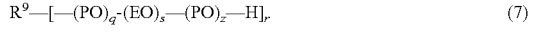
$$R^9-[-(PO)_q-(EO)_s-(PO)_z-H]_r \quad (7)$$

$R^5$, $R^6$, $R^7$, $R^8$ and $R^9$ are a hydroxyl group or a reaction residue of an active hydrogen compound having a carbon number of 1 to 25, PO is an oxypropylene group, EO is an oxyethylene group, q, s, t and z are an integer of 1 to 100, and r is an integer of 1 to 10. The oxyethylene group and the oxypropylene group in the general formulae (4), (5), (6) and (7) are bound in a block form.

Among $R^5$, $R^6$, $R^7$, $R^8$ and $R^9$, the reaction residue of an active hydrogen compound having a carbon number of 1 to 25 means a reaction residue formed by excluding an active hydrogen from the active hydrogen compound having a carbon number of 1 to 25.

Examples of the active hydrogen-containing compound having a carbon number of 1 to 25 include compounds containing at least one hydroxyl group (—OH), imino group (—NH—), amino group (—NH$_2$) and/or carboxyl group (—COOH), that is, an alcohol, an amide, an amine, a carboxylic acid, a hydroxycarboxylic acid, and an aminocarboxylic acid.

Examples of the alcohol include monools (methanol, butanol, stearyl alcohol, oleyl alcohol, isostearyl alcohol, etc.), polyols (ethylene glycol, propylene glycol, glycerin, diglycerin, tetraglycerin, trimethylol propane, pentaerythritol, dipentaerythritol, dihydroxyacetone, fructose, glucose, mannose, galactose, sucrose, lactose, trehalose, etc.), and the like.

Examples of the amide include monoamides (formic acid amide, propionic acid amide, stearylamide, etc.), polyamides (malonic acid diamide, ethylene bis-octylamine, etc.), and the like.

Examples of the amine include monoamines (dimethylamine, ethylamine, aniline, stearylamine, etc.), polyamines (ethylenediamine, diethylenetriamine, triethylenetetramine, etc.), and the like.

Examples of the carboxylic acid include monocarboxylic acids (acetic acid, stearic acid, oleic acid, benzoic acid, etc.), polycarboxylic acids (maleic acid, hexanedioic acid, etc.), and the like.

Examples of the hydroxycarboxylic acid include hydroxyacetic acid, tartaric acid, malic acid, 12-hydroxystearic acid, and the like.

Examples of the aminocarboxylic acid include glycine, 4-aminobutyric acid, 6-aminohexanoic acid, 12-aminolauric acid, and the like.

q, s, t and z are an integer of 1 to 100, preferably an integer of 2 to 75, and further preferably an integer of 3 to 60.

r is an integer of 1 to 10, preferably an integer of 1 to 7, and further preferably an integer of 1 to 5.

Among them, the polyoxypropylene polyol (B1) represented by the general formula (3) and the polyoxyethylene polyoxypropylene polyol (B4) represented by the general formula (6) are preferred, from the viewpoint of production efficiency.

The content of the polyoxyalkylene compound (A) is preferably 10 to 99.9% by weight, further preferably 15 to 90% by weight, and particularly preferably 20 to 80% by weight, based on the total weight of the polyoxyalkylene compound (A) and the polyoxyalkylene polyol (B). The content of the polyoxyalkylene polyol (B) is preferably 0.1 to 90% by weight, further preferably 10 to 85% by weight, and particularly preferably 20 to 80% by weight, based on the total weight of the polyoxyalkylene compound (A) and the polyoxyalkylene polyol (B).

The additives for a bioethanol fermentation process of the present invention can be obtained by applying a known production method.

The polyoxyalkylene compound (A) and the polyoxyalkylene polyol (B) can be produced by a known alkylene oxide addition reaction and an etherification reaction. Then, the polyoxyalkylene compound (A) and the polyoxyalkylene polyol (B) are uniformly mixed to obtain the additive for a bioethanol fermentation process of the present invention.

The temperature and time of the uniform mixing are not particularly limited so long as the compounds can be uniformly mixed, but are preferably 5 to 60° C. and 10 minutes to 5 hours. Also, there is no particular restriction on the mixing device for uniformly mixing the compounds, and a blade type stirrer, a line mixer or the like can be used.

As a raw material which can be used in the method for producing bioethanol of the present invention, at least one selected from the group consisting of saccharide raw materials, starch raw materials and wooden (or cellulose) raw materials can be used.

The saccharide raw materials are food resources containing much saccharide, and examples include sugar cane, molasses, sugar beet, and the like.

The starch raw materials are food resources containing much starch, and examples include corn, sorghum, potato, sweet potato, wheat, and the like.

The wooden (or cellulose) raw materials are inedible food resources containing much cellulose, and examples include woods, waste building materials, and the like. As the wood, in addition to coniferous trees (pine, fir, hemlock, spruce, larch, radiata pine, etc.) and broadleaf trees (eucalyptus, poplar, beech, maple, birch, etc.), kenaf, paper bush, paper mulberry, Diplomorpha, mulberry, Manila hemp, reed, bamboo and the like are included. These woods may be thinnings, lumber waste, driftwood and pruned branches, and may contain the branches of woods, roots and leaves. The waste building materials include waste wooden building materials, waste wooden pallets, waste wooden packing materials, and the like.

As the method for producing bioethanol of the present invention, known methods can be applied, and examples include saccharification pretreatment process, saccharification process, and ethanol fermentation process.

In the ethanol fermentation process, the additive for a bioethanol fermentation process is added to a fermentation liquid, and then fermented.

The amount of the additive for a bioethanol fermentation process added is not particularly limited, and is preferably about 0.0001 to 5% by weight, based on the weight of the fermentation liquid.

The fermentation liquid passed through the ethanol fermentation process is subjected to a separation process of separating the produced ethanol. As a method for separating ethanol, a known method such as distillation method and pervaporation membrane method can be used. Ethanol obtained by separation may be used as it is, or may be used after purification by a known method such as distillation.

EXAMPLES

Hereinbelow, the present invention will be described further in detail with reference to examples, but the present invention is not limited thereto. Unless otherwise indicated, parts mean parts by weight, and % means % by weight.

Polyoxyalkylene compounds (a11 to a16, a21 to a27) and polyoxyalkylene polyols (b31 to b37, b41 to b43, b51 to b53, b61 to b67, and b71 to b73) synthesized by known methods are shown in Tables 1 to 3. In the tables, EO represents oxyethylene, PO represents ox propylene, and BO represents oxybutylene.

TABLE 1

$R^1O-(AO)_m-R^2$ (1)

| | $R^1$ | $(AO)_m$ | $R^2$ | HLB |
|---|---|---|---|---|
| a11 | Butyl | $(PO)_{60}$ | Lignoceryl | 0 |
| a12 | Cetyl | $(PO)_{14}$ | Hydrogen atom | 0 |
| a13 | Montanyl | $(BO)_1$ | Methyl | 0 |
| a14 | Myristyl | $(PO)_{14}$ | Hydrogen atom | 0 |
| a15 | Butyl | $(PO)_{100}$ | Hydrogen atom | 0 |
| a16 | Cetyl | $(PO)_3$ | Hydrogen atom | 0 |

TABLE 2

$R^3O-(AO)_n-(EO)_p-R^4$ (2)

| | $R^3$ | $(AO)_n$ | p | $R^4$ | HLB |
|---|---|---|---|---|---|
| a21 | Montanyl | $(PO)_{10}$ | 10 | Ethyl | 6 |
| a22 | Cetyl | $(PO)_{14}$ | 6 | Hydrogen atom | 4 |
| a23 | Butyl | $(PO)_{100}$ | 3 | Methyl | 0.4 |
| a24 | Myristyl | $(PO)_{14}$ | 4 | Hydrogen atom | 2.9 |
| a25 | Cetyl | $(BO)_1$ | 3 | Lignoceryl | 3.3 |
| a26 | Myristyl | $(PO)_3$ | 3 | Hydrogen atom | 5.1 |
| a27 | Butyl | $(PO)_{60}$ | 7 | Hydrogen atom | 1.6 |

TABLE 3

| | Structural formula |
|---|---|
| b31 | HO—[—$(PO)_{30}$—H]$_1$ |
| b32 | HO—[—$(PO)_{34}$—H]$_1$ |
| b33 | (Glyceryl)-[—$(PO)_{16}$—H]$_3$ |
| b34 | (Glyceryl)-[—$(PO)_2$—H]$_3$ |
| b35 | (Stearyl)-[—$(PO)_{75}$—H]$_1$ |
| b36 | $C_{17}H_{35}COO$—[—$(PO)_{15}$—H]$_1$ |
| b37 | $CH_3CH_2N$—[—$(PO)_3$—H]$_2$ |
| b41 | (Methyl)-[—$(EO)_{60}$—$(PO)_{70}$—H]$_1$ |
| b42 | HO—[—$(EO)_3$—$(PO)_{60}$—H]$_1$ |
| b43 | $C_2H_5C(=O)N$—[—$(EO)_7$—$(PO)_3$—H]$_2$ |
| b51 | (Lignoceryl)—[—$(PO)_3$—$(EO)_3$—H]$_1$ |
| b52 | HO—[—$(PO)_{60}$—$(EO)_{60}$—H]$_1$ |
| b53 | $CH_3CH_2N$—[—$(PO)_3$—$(EO)_3$—H]$_2$ |
| b61 | HO—[—$(EO)_3$—$(PO)_{37}$—$(EO)_8$—H]$_1$ |
| b62 | HO—[—$(EO)_3$—$(PO)_{37}$—$(EO)_3$—H]$_1$ |
| b63 | HO—[—$(EO)_{60}$—$(PO)_{37}$—$(EO)_{60}$—H]$_1$ |
| b64 | (Glyceryl)-[—$(EO)_7$—$(PO)_3$—$(EO)_3$—H]$_3$ |
| b65 | (Stearyl)-[—$(EO)_7$—$(PO)_{60}$—$(EO)_3$—H]$_1$ |
| b66 | $C_{17}H_{35}COO$—[—$(EO)_2$—$(PO)_8$—$(EO)_2$—H]$_1$ |
| b67 | $CH_3CH_2N$—[—$(EO)_3$—$(PO)_5$—$(EO)_3$—H]$_2$ |
| b71 | $CH_3CH_2N$—[—$(PO)_{50}$—$(EO)_8$—$(PO)_3$—H]$_2$ |
| b72 | HO—[—$(PO)_3$—$(EO)_3$—$(PO)_{60}$—H]$_1$ |
| b73 | (Stearyl)-[—$(PO)_3$—$(EO)_{60}$—$(PO)_3$—H]$_2$ |

Example 1

The polyoxyalkylene compound a11 [9 parts] and the polyoxyalkylene compound a21 [1 part] were uniformly mixed by stirring at 30° C. for 30 minutes by a blade-type stirrer, then the polyoxyalkylene polyol b31 [90 parts] was added to this mixture, and the mixture was uniformly mixed by stirring at 30° C. for 1 hour to obtain an additive 1 for a bioethanol fermentation process of the present invention.

Examples 2 to 27

The same procedures were carried out as in Example 1, except for changing the polyoxyalkylene compound a11 [9 parts], the polyoxyalkylene compound a21 [1 part] and the polyoxyalkylene polyol b31 [90 parts] to the polyoxyalkylene compounds and polyoxyalkylene polyols (the type and the number of parts) shown in Table 4 to obtain the additives 2 to 27 for a bioethanol fermentation process of the present invention.

TABLE 4

| | | Polyoxyalkylene compound (A) | | | | Polyoxyalkylene polyol (B) | |
| --- | --- | --- | --- | --- | --- | --- | --- |
| | | (A1) | | (A2) | | | |
| | | Type | Number of parts | Type | Number of parts | Type | Number of parts |
| Examples | 1 | a11 | 9 | a21 | 1 | b31 | 90 |
| | 2 | a12 | 35 | a22 | 35 | b32 | 30 |
| | 3 | a13 | 0.9 | a23 | 89.1 | B33 | 10 |
| | 4 | a11 | 70 | — | — | b41 | 30 |
| | 5 | — | — | a21 | 70 | b51 | 30 |
| | 6 | a12 | 35 | a22 | 35 | b61 | 30 |
| | 7 | a13 | 35 | a23 | 35 | b71 | 30 |
| | 8 | a14 | 35 | a24 | 35 | b32 | 30 |
| | 9 | a15 | 5 | a25 | 10 | b32 | 85 |
| | 10 | a16 | 59.5 | a26 | 10.5 | b33 | 30 |
| | 11 | a11 | 35 | a27 | 35 | b33 | 30 |
| | 12 | a11 | 35 | a21 | 35 | b34 | 30 |
| | 13 | a12 | 35 | a22 | 35 | b35 | 30 |
| | 14 | a13 | 35 | a23 | 35 | b36 | 30 |
| | 15 | a14 | 35 | a24 | 35 | b37 | 30 |
| | 16 | a11 | 35 | a21 | 35 | b42 | 30 |
| | 17 | a12 | 35 | a22 | 35 | b43 | 30 |
| | 18 | a13 | 35 | a23 | 35 | b52 | 30 |
| | 19 | a14 | 35 | a24 | 35 | b53 | 30 |
| | 20 | a11 | 35 | a21 | 35 | b64 | 30 |
| | 21 | a12 | 35 | a22 | 35 | b65 | 30 |
| | 22 | a13 | 35 | a23 | 35 | b66 | 30 |
| | 23 | a14 | 35 | a24 | 35 | b67 | 30 |
| | 24 | a11 | 35 | a21 | 35 | b72 | 30 |
| | 25 | a12 | 35 | a22 | 35 | b73 | 30 |
| | 26 | a13 | 35 | a23 | 35 | b62 | 30 |
| | 27 | a14 | 35 | a24 | 35 | b63 | 30 |

Using the additives for a bioethanol fermentation process obtained in Examples 1 to 27, the production efficiency test was carried out as follows, and the results are shown in Table 5. As a blank, the results of testing without using the additive for a bioethanol fermentation process are also shown in Table 5.

<Production Efficiency Test>

Since the production efficiency of bioethanol fermentation in laboratory levels cannot be compared, the following accelerated test was performed.

100 mL of a bioethanol fermentation liquid created by diluting 200 parts of commercially available sugar cane molasses (purchased from MARUKYG NOSAN CO., LTD.) with 800 parts of ion-exchanged water was put in a glass graduated cylinder with an inner diameter of 50 mm×height of 350 mm, 17 μL of a measurement sample (additive for a bioethanol fermentation process) was added with a microsyringe, and a diffuser stone was inserted into the bottom of the liquid, then carbon dioxide gas was bubbled at 500 mL/min. The volume (mL) of the bioethanol fermentation liquid after 10 minutes was read, and the production efficiency (%) was calculated from the following equation. The smaller the value, the size of the fermenter to be used in the production can be reduced, and the production efficiency is improved.

Production efficiency (%)=(Volume of bioethanol fermentation liquid after 10 minutes)/100

TABLE 5

| | | HLB of polyoxyalkylene compound (A) | Production efficiency (%) |
| --- | --- | --- | --- |
| Example | 1 | 0 and 6 | 180 |
| | 2 | 0 and 4 | 135 |
| | 3 | 0 and 0.4 | 195 |
| | 4 | 0 | 300 |
| | 5 | 6 | 280 |
| | 6 | 0 and 4 | 150 |
| | 7 | 0 and 0.4 | 200 |
| | 8 | 0 and 2.9 | 125 |
| | 9 | 0 and 3.3 | 205 |
| | 10 | 0 and 5.1 | 130 |
| | 11 | 0 and 1.6 | 185 |
| | 12 | 0 and 6 | 150 |
| | 13 | 0 and 4 | 135 |
| | 14 | 0 and 0.4 | 155 |
| | 15 | 0 and 2.9 | 130 |
| | 16 | 0 and 6 | 180 |
| | 17 | 0 and 4 | 170 |
| | 18 | 0 and 0.4 | 185 |
| | 19 | 0 and 2.9 | 165 |
| | 20 | 0 and 6 | 155 |
| | 21 | 0 and 4 | 140 |
| | 22 | 0 and 0.4 | 145 |
| | 23 | 0 and 2.9 | 140 |
| | 24 | 0 and 6 | 170 |
| | 25 | 0 and 4 | 180 |
| | 26 | 0 and 0.4 | 140 |
| | 27 | 0 and 2.9 | 185 |
| Blank | | — | 600< |

The additive for a bioethanol fermentation process of the present invention had extremely good production efficiency, as compared to those not using the additive for a bioethanol fermentation process (blank).

INDUSTRIAL APPLICABILITY

The additive for a bioethanol fermentation process of the present invention is suitable as an additive for improving the production efficiency of bioethanol.

The invention claimed is:

1. An additive for a bioethanol fermentation process comprising:
   a polyoxyalkylene compound (A) comprising a mixture of a polyoxyalkylene alkyl compound (A1) represented by general formula (1) and a polyoxyalkylene alkyl compound (A2) represented by general formula (2);

$$R^1O\text{-}(AO)_m\text{—}R^2 \quad (1)$$

$$R^3O\text{-}(AO)_n\text{-}(EO)_p\text{—}R^4 \quad (2)$$

wherein $R^1$ and $R^3$ represent an alkyl group or alkenyl group having a carbon number of 4 to 28, $R^2$ and $R^4$ represent a hydrogen atom or a monovalent organic group having a carbon number of 1 to 24, AO represents an oxyalkylene group having a carbon number of 3 to 18, or a reaction residue of glycidol or an alkyl glycidyl ether or alkenyl glycidyl ether having a carbon number of 4 to 21, EO represents an oxyethylene group, m and n are an integer of 1 to 100, and p is an integer of 3 to 10; and
   a polyoxyalkylene polyol (B),
   wherein the content of the polyoxyalkylene compound (A) is 10 to 99.9% by weight, and the content of the polyoxyalkylene polyol (B) is 0.1 to 90% by weight, based on the total weight of the polyoxyalkylene compound (A) and the polyoxyalkylene polyol (B).

2. The additive according to claim 1, wherein the polyoxyalkylene compound (A) has a Griffin's HLB value in the range of 0 to 6.

3. The additive according to claim 1, wherein the polyoxyalkylene polyol (B) is at least one selected from the group consisting of a polyoxypropylene polyol (B1) represented by a general formula (3), a polyoxyethylene polyoxypropylene polyol (B2) represented by a general formula (4), a polyoxyethylene polyoxypropylene polyol (B3) represented by a general formula (5), a polyoxyethylene polyoxypropylene polyol (B4) represented by a general formula (6), and a polyoxyethylene polyoxypropylene polyol (B5) represented by a general formula (7);

$$R^5-[-(PO)_q-H]_r \qquad (3)$$

$$R^6-[-(EO)_s-(PO)_q-H]_r \qquad (4)$$

$$R^7-[-(PO)_q-(EO)_s-H]_r \qquad (5)$$

$$R^8-[-(EO)_s-(PO)_q-(EO)_t-H]_r \qquad (6)$$

$$R^9-[-(PO)_q-(EO)_s-(PO)_z-H]_r \qquad (7)$$

wherein $R^5$, $R^6$, $R^7$, $R^8$ and $R^9$ are a hydroxyl group or a reaction residue of an active hydrogen compound having a carbon number of 1 to 25, PO is an oxypropylene group, EO is an oxyethylene group, q, s, t and z are an integer of 1 to 100, and r is an integer of 1 to 10; and the oxyethylene group and the oxypropylene group in the general formulae (4), (5), (6) and (7) are bound in a block form.

4. The additive according to claim 1, wherein the content of the polyoxyalkylene alkyl compound (A1) represented by the general formula (1) is 0.1 to 90% by weight, and the content of the polyoxyalkylene alkyl compound (A2) represented by the general formula (2) is 10 to 99.9% by weight, based on the weight of the polyoxyalkylene compound (A).

5. A method for producing bioethanol in which at least one selected from the group consisting of saccharide raw materials, starch raw materials and wooden (or cellulose) raw materials is used as a raw material, the method comprising:
a fermentation step of fermenting the raw material by adding the additive as defined in claim 1 to a fermentation liquid.

* * * * *